(12) United States Patent
Hunter et al.

(10) Patent No.: US 6,545,051 B1
(45) Date of Patent: Apr. 8, 2003

(54) ANTIBACTERIAL HYDROXAMIC ACID DERIVATIVES

(75) Inventors: Michael George Hunter, Oxford (GB); Raymond Paul Beckett, Oxford (GB); John Martin Clements, Oxford (GB); Mark Whittaker, Oxford (GB)

(73) Assignee: British Biotech Pharmaceuticals, Ltd., Oxford (GB)

( * ) Notice: Subject to any disclaimer, the term of this patent is extended or adjusted under 35 U.S.C. 154(b) by 0 days.

(21) Appl. No.: 09/889,801

(22) PCT Filed: Jan. 27, 2000

(86) PCT No.: PCT/GB00/00233

§ 371 (c)(1), (2), (4) Date: Jul. 20, 2001

(87) PCT Pub. No.: WO00/44373

PCT Pub. Date: Aug. 3, 2000

(30) Foreign Application Priority Data

Jan. 29, 1999 (GB) ............................................. 9901863

(51) Int. Cl.⁷ ............................................. A61K 31/19
(52) U.S. Cl. ............................................. 514/575
(58) Field of Search ............................................. 514/575

(56) References Cited

U.S. PATENT DOCUMENTS

| 5,652,262 A | * | 7/1997 | Crimmin et al. ............ 514/507 |
| 5,821,262 A | * | 10/1998 | Crimmin et al. ............ 514/445 |
| 5,861,436 A | * | 1/1999 | Beckett et al. ............... 514/575 |

FOREIGN PATENT DOCUMENTS

| EP | 0 423 943 | 4/1991 |
| JP | 03 157372 | 7/1991 |
| WO | WO 97/49674 | 12/1997 |
| WO | WO 98/11063 | 3/1998 |
| WO | WO 99/40910 | 8/1999 |
| WO | WO 99/44602 | 9/1999 |
| WO | WO 99/46241 | 9/1999 |

\* cited by examiner

Primary Examiner—Kevin E. Weddington
(74) Attorney, Agent, or Firm—Banner & Witcoff, Ltd.

(57) ABSTRACT

A method for the treatment of bacterial infections in humans and non-human mammals, which comprises administering to a subject suffering such infection an antibacterial effective dose of a compound of formula (I):

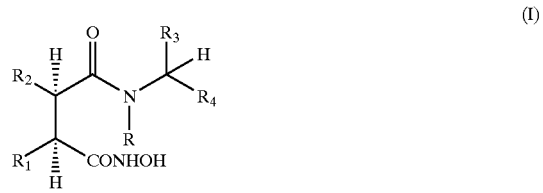

wherein $R_1$ represents hydrogen, hydroxy, amino, methyl, or trifluoromethyl; $R_2$ represents a group $R_{10}$—$(X)_n$—(ALK)— wherein $R_{10}$ represents hydrogen, a $C_1$–$C_6$ alkyl, $C_2$–$C_6$ alkenyl, $C_2$–$C_6$ alkynyl, cycloalkyl, aryl, or heterocyclyl group, ALK represents a straight or branched divalent $C_1$–$C_6$ alkylene, $C_2$–$C_6$ alkenylene, $C_2$–$C_6$ alkynylene radical, and may be interrupted by one or more non-adjacent —NH—, —O— or —S— linkages; X represents —NH—, —O— or —S—, and n is 0 or 1; R represents hydrogen or $C_{1-C6}$ alkyl; $R_3$ represents the characterising group of a natural or non-natural α amino acid in which any functional groups may be protected; and $R_4$ represents an ester or thioester group.

14 Claims, No Drawings

ANTIBACTERIAL HYDROXAMIC ACID DERIVATIVES

This invention relates to the use of hydroxamic acid derivatives as antibacterial agents.

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as Staphylococci, Streptococci, Mycobacteria and Enterococci, resistant strains have evolved/arisen which makes them particularly difficult to eradicate. Examples of such strains are methicillin resistant *Staphylococcus aureus* (MRSA), methicillin resistant coagulase negative Staphylococci (MRCNS), penicillin resistant *Streptococcus pneumoniae* and multiply resistant *Enterococcus faecium*.

Pathogenic bacteria are often resistant to the aminoglycoside, β-lactam (penicillins and cephalosporins), and chhloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849–62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylocccus aureus*, is of utmost importance.

The natural antibiotic actinonin (see for example J. C. S Perkin I, 1975, 819) is a hydroxamic acid derivative of Structure (A):

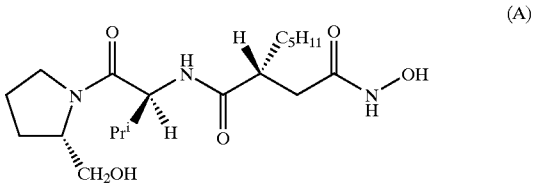

(A)

In ddition to actinonin, various structural analogues of actinonin have also been shown to have antibacterial activity (see for example Broughton et al. (Devlin et al. Journal of the Chemical Society. Perkin Transactions 1 (9):830–841, 1975; Broughton et al. Journal of the Chemical Society. Perkin Transactions 1 (9):857–860, 1975).

The matlystatin group of compounds, share a number of structural similarities with actinonin. Both are peptidic molecules with functional hydroxamic acid metal binding groups (Ogita et al., J. Antibiotics. 45(11):1723–1732; Tanzawa et al., J. Antibiotics. 45(11):1733–1737; Haruyama et al., J. Antibiotics. 47(12):1473–1480; Tamaki et al., J. Antibiotics. 47(12):1481–1492).

Since this invention is concerned with the use of hydroxamic acid derivatives, it is noted that many hydroxamic acid derivatives have previously been disclosed as inhibitors of matrix metalloproteinases (MMP), enkephalinase, angiotensin and other natural enzymes which play various roles in several human disease states. (For a review of the compounds known in the MMP inhibitor context, see Beckett, Exp. Opin. Ther. Patents (1996) 6:1305–1315 and Beckett & Whittaker, Ibid. (1998) 8(3):250–282). However, it appears the only hydroxamic acid derivatives previously disclosed as having antibacterial activity are the actinonin and matlystatin classes referred to above.

BRIEF DESCRIPTION OF THE INVENTION

WO 98/11063 and WO 99/46241 (British Biotech) disclose the use of certain ester and thioester compounds containing a hydroxamic acid group as inhibitors of the proliferation of rapidly dividing tumour cells, and claim that use together with a class of such esters and thioesters per se. This invention is based on the finding that a subset of the ester and thioester compounds containing a hydroxamic acid group with which WO 98/11063 and WO 99/46241 are concerned have antibacterial activity, against members of the Gram-positive and/or Gram-negative classes.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes the methionyl moiety carried by the initiator tRNA is N-formylated prior to its incorporation into a polypeptide. Consequently, N-formylmethionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607–614, 1999). Deformylation is, therefore, a crucial step in bacterial protein biosynthesis and the enzyme responsible, PDF, is essential for normal bacterial growth. Although the gene encoding PDF (def) is present in all pathogenic bacteria for which sequences are known (Meinnel et al., J. Mol. Biol, 266:939–49, 1997), it has no eukaryotic counterpart, making it an attractive target for antibacterial chemotherapy.

The isolation and characterisation of PDF has been facilitated by an understanding of the importance of the metal ion in the active site (Groche et al., Biophys. Biochem. Res. Commun., 246:324–6, 1998). The $Fe^{2+}$ form is highly active in vivo but is unstable when isolated due to oxidative degradation (Rajagopalan et al., J. Biol. Chem. 273:22305–10, 1998). The $Ni^{2+}$ form of the enzyme has specific activity comparable with the ferrous enzyme but is oxygen-insensitive (Ragusa et al., J. Mol. Biol. 1998, 280:515–23, 1998); The $Zn^{2+}$ enzyme is also stable but is almost devoid of catalytic activity (Rajagopalan et al., J. Am. Chem. Soc. 119:12418–12419, 1997).

Several X-ray crystal structures and NMR structures of *E. coli* PDF, with or without bound inhibitors, have been published (Chan et al., Biochemistry 36:13904–9, 1997; Becker et al., Nature Struct. Biol. 5:1053–8, 1998; Becker et al., J. Biol. Chem. 273:11413–6, 1998; Hao et al., Biochemistry, 38:4712–9, 1999; Dardel et al., J. Mol. Biol. 280:501–13, 1998; O'Connell et al., J. Biomol. NMR, 13:311–24, 1999), indicating similarities in active site geometry to metalloproteinases such as thermolysin and the metzincins.

Recently the substrate specificity of PDF has been extensively studied (Ragusa et al., J. Mol. Biol. 289:1445–57, 1999; Hu et al., Biochemistry 38:643–50,1999; Meinnel et al., Biochemistry, 38:4287–95, 1999). These authors conclude that an unbranched hydrophobic chain is preferred at P1', while a wide variety of P2' substituents are acceptable and an aromatic substituent may be advantageous at the P3' position. There have also been reports that small peptidic compounds containing an H-phosphonate (Hu et al., Bioorg. Med. Chem. Lett., 8:2479–82, 1998) or thiol (Meinnel et al., Biochemistry, 38:4287–95, 1999) metal binding group are micromolar inhibitors of PDF. Peptide aldehydes such as calpeptin. (N-Cbz-Leu-norleucinal) have also been shown to inhibit PDF (Durand et al., Arch. Biochem. Biophys., 367:297–302, 1999). However, the identity of the metal binding group and its spacing from the rest of the molecule ("recognition fragment") has not been studied extensively. Furthermore, non-peptidic PDF inhibitors, which may be desirable from the point of view of bacterial cell wall permeability or oral bioavailability in the host species, have not been identified.

DETAILED DESCRIPTION OF THE INVENTION

According to the first aspect of the present invention there is provided the use of a compound of formula.(I),or a pharmaceutically or veterinarily acceptable salt, hydrate or solvate thereof in the preparation of an antibacterial composition:

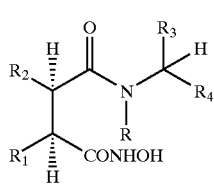

(I)

wherein:
$R_1$ represents hydrogen, hydroxy, amino, methyl, or trifluoromethyl
$R_2$ represents a group $R_{10}$—$(X)_n$—(ALK)— wherein
$R_{10}$ represents hydrogen, a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo (including fluoro, chloro, bromo, and iodo), trifluoromethyl, cyano, nitro, —COOH, —$CONH_2$, —$COOR^A$, —$NHCOR^A$, —$CONHR^A$, —$NHR^A$,—$NR^AR^B$, or —$CONR^AR^B$ wherein $R^A$ and $R^B$ are independently a ($C_1$–$C_6$)alkyl group, and
ALK represents a straight or branched.divalent $C_1$–$C_6$ alkylene, $C_2$–$C_6$ alkenylene, $C_2$–$C_6$ alkynylene radical, and may be interrupted by one or more non-adjacent —NH—, —O— or —S— linkages,
X represents —NH—, —O— or —S—, and
n is 0 or 1;
R represents hydrogen or $C_1$–$C_6$ alkyl,
$R_3$ represents the characterising group of a natural or non-natural α amino acid in which any functional groups may be protected; and
$R_4$ represents an ester or thioester group,
or a pharmaceutically acceptable salt, hydrate or solvate thereof.

In another aspect, the invention provides a method for the treatment of bacterial infections in humans and non-human mammals,.which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above.

In a further aspect of the invention there is provided a pharmaceutical or veterinary composition comprising a compound as defined by reference to formula (I) above, together with a pharmaceutically or veterinarily acceptable excipient or carrier.

Compositions of the invention may additionally include an antibacterial agent other than one defined by reference-to formula (I) above.

In addition to their pharmaceutical or veterinary use, the compounds of the invention may also be of use as component(s) of general antibacterial cleaning or disinfecting materials.

As used herein the term ($C_1$–$C_6$)alkyl means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent ($C_1$–$C_6$)alkylene radical" means a saturated hydrocarbon chain having from 1 to 6 carbon atoms and two unsatisfied valencies.

As used herein the term ($C_2$–$C_6$)alkenyl means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent $(C_2–C_6)$alkenylene radical" means a hydrocarbon chain having from 2 to 6 carbon atoms, at least one double bond, and two unsatisfied valencies.

As used herein the term "$C_2–C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_2–C_6)$alkynylene radical" means a hydrocarbon chain having from 2 to 6 carbon atoms, at least one triple bond, and two unsatisfied valencies.

As used herein the term cycloalkyl means a saturated alicyclic moiety having from 3–8 carbon atoms and includes, for example, cyclopropyl, cyclobutyl, cyclopentyl, cyclohexyl, cycloheptyl and cyclooctyl.

As used herein the term cycloalkenyl means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

As used herein the term "aryl" -refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms, and optionally fused to a benzyl or pyridyl ring; and to groups consisting of two covalently linked 5- or 6-membered aromatic rings each containing one or more heteroatoms; and to groups consisting of a monocyclic carbocyclic aromatic group covalently linked to a 5- or 6-membered aromatic rings containing one or more heteroatoms. Illustrative of such groups are thienyl, furyl, pyrrolyl, imidazolyl benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term heterocyclyl or heterocyclic includes "heteroaryl" as defined above, and in particular means a 5–7 membered aromatic or non-armoatic heterocyclic-ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido and 1,3-dioxo-1,3-dihydro-isoindol-2-yl groups.

The term "ester" or "esterified carboxyl group" means a group $R_9O(C=O)$— in which $R_9$ is the group characterising the ester, notionally derived from the alcohol $R_9OH$.

The term "thioester" means a group $R_9S(C=O)$— or $R_9S(C=S)$— or $R_9O(C=S)$— in which $R_9$ is the group characterising the thioester, notionally derived from the alcohol $R_9OH$ or the thioalcohol $R_9SH$.

Unless otherwise specified in the context in which it occurs, the term substituted as applied to any moiety herein means substituted with up to four substituents, each of which independently may be $(C_1–C_6)$alkyl, $(C_1–C_6)$alkoxy, phenoxy, hydroxy, mercapto, $(C_1–C_6)$alkylthio, amino, halo (including fluoro, chloro, bromo and iodo), trifluoromethyl, nitro, —COOH, —CONH$_2$, —COOR$^A$, —NHCOR$^A$, —CONHR$^A$, NHR$^A$, —NR$^A$R$^B$, or —CONR$^A$R$^B$ wherein $R^A$ and $R^B$ are independently a $(C_1–C_6)$alkyl group.

As used herein the terms side chain of a natural alpha-amino acid and side chain of a non-natural alpha-amino acid mean the group $R^X$ in respectively a natural and non-natural amino acid of formula NH$_2$—CH(R$^X$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example aminb, carboxyl, hydroxy, mercapto, guanidyl, imidazolyl, or indolyl groups as in arginine, lysine, glutamic acid, aspartic acid, tryptophan, histidine, serine, threonine, tyrosine, and-cysteine, such functional substituents may optionally be protected.

Likewise, the side chains of-non-natural alpha amino acids which contain functional substituents, for example amino, carboxyl, hydroxy, mercapto, guanidyl, imidazolyl, or indolyl groups, such functional substituents may optionally be protected.

The term protected when used in relation to a functional substituent in a side chain of a natural or non-natural alpha-amino acid means a derivative of such a substituent which is substantially non-functional. For example, carboxyl groups may be esterified (for example as a $C_1–C_6$ alkyl ester), amino groups may be converted to amides (for example as a NHCOC$_1$–C$_6$alkyl amide) or carbamates (for example as an NHC(=O)OC$_1$–C$_6$ alkyl or NHC(=O) OCH$_2$Ph carbamate), hydroxyl groups may be converted to ethers (for example an OC$_1$–C$_6$ alkyl or a O(C$_1$–C$_6$ alkyl) phenyl ether) or esters (for example a OC(=O)C$_1$–C$_6$ alkyl ester) and thiol groups may be converted to thioethers (for example a tert-butyl or benzyl thioether) or thioesters (for example a SC(=O)C$_1$–C$_6$ alkyl thioester).

There are several actual or potential chiral centres in the compounds according to the invention because of the presence of asymmetric carbon atoms. The presence of several asymmetric carbon atoms gives rise to a number of diastereomers with R or S stereochemistry at each chiral centre. The invention includes all such diastereomers and mixtures thereof. Presently it is preferred that the stereochemical configuration at the carbon atom carrying the $R_2$ group is R, and the configuration of the carbon atom carrying the $R_3$ group is S.

In the compounds for use according to the invention:

Presently, it is preferred that $R_1$ is hydrogen.

$R_2$ may be, for example:

$C_1–C_6$ alkyl, $C_3–C_6$ alkenyl or $C_3–C_6$ alkynyl;

phenyl($C_1–C_6$ alkyl)-, phenyl($C_3–C_6$ alkenyl)- or phenyl ($C_3–C_6$ alkynyl)- optionally substituted in the phenyl ring;

cycloalkyl($C_1–C_6$ alkyl)-, cycloalkyl($C_3–C_6$ alkenyl)- or cycloalkyl($C_3–C_6$ alkynyl)- optionally substituted in the phenyl ring;

heterocyclyl($C_1–C_6$ alkyl)-, heterocyclyl($C_3–C_6$ alkenyl)- or heterocyclyl($C_3–C_6$ alkynyl)- optionally substituted in the heterocyclyl ring;

4-phenylphenyl($C_1$–$C_6$ alkyl)-, 4-phenylphenyl($C_3$–$C_6$ alkenyl)-, 4-phenylphenyl($C_3$–$C_6$ alkynyl)- 4-heteroarylphenyl($C_1$–$C_6$ alkyl)-, 4-heteroarylphenyl ($C_3$–$C_6$ alkenyl)-, 4-heteroarylphenyl($C_3$–$C_6$ alkynyl)-, optionally substituted in the terminal phenyl or heteroaryl ring;

Specific examples of such groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups, at $R_2$ are n-propyl, n-butyl, n-pentyl, benzyl and cyclopentylmethyl R may be, for example, hydrogen or methyl, with hydrogen being presently preferred.

$R_3$ may be, for example $C_1$–$C_6$ alkyl, phenyl, 2,- 3-, or 4-hydroxyphenyl, 2,- 3-, or 4-methoxyphenyl, 2,- 3-, or 4-pyridylmethyl, 2,- 3-, or 4-hydroxybenzyl, 2,- 3-, or 4-benzyloxybenzyl, 2,- 3-, or 4-$C_1$–$C_6$ alkoxybenzyl, or benzylbxy($C_1$–$C_6$alkyl)- group; or the characterising group of a natural α amino acid, for example benzyl, isopropyl, isobutyl, methyl or 4-methoxyphenylmethyl, in which any functional group may be protected, any amino group may be acylated and any carboxyl group present may be amidated; or a group -[Alk]$_n$$R_7$ where Alk is a ($C_1$–$C_6$)alkyl or ($C_2$–$C_6$) alkenyl group optionally interrupted by one or more —O—,or —S— atoms or —N($R_{12}$)— groups [where $R_{12}$ is a hydrogen atom or a ($C_1$–$C_6$)alkyl group], n is 0 or 1, and $R_7$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:
each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or $R_c$ is hydrogen and $R_a$ and $R_b$ are independently phenyl or heteroaryl such as pyridyl; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_{1-C4}$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —SO$_2$($C_1$–$C_6$)alkyl, —S($C_2$–$C_6$) alkenyl, —SO($C_2$–$C_6$)alkenyl, —SO$_2$($C_2$–$C_6$) alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH($C_1$–$C_6$) alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$ ($C_1$–$C_6$)alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$)alkyl, ($C_2$–$C^6$)alkenyl, ($C_2$–$C_6$)alkynyl, ($C_3$–$C_8$)cycloalkyl, ($C_4$–$C_8$)cycloalkenyl, phenyl or benzyl.

Examples of particuiar $R_3$ groups include benzyl, phenyl, cyclohexylmethyl, pyridin-3-ylmethyl, tert-butoxymethyl, n-propyl, iso-propyl, iso-butyl, sec-butyl, tert-butyl, 1-benzylthio-1-methylethyl, 1-methylthio-1-methylethyl, and 1-mercapto-1-methylethyl Presently preferred $R_3$ groups include methyl benzyl, tert-butyl, iso-butyl, phenyl and isopropyl.

Examples of particular ester and thioester groups $R_4$ groups include those of formula —(C=O)OR$_9$, —(C=O) SR$_9$, —(C=S)SR$_9$, and —(C=S)OR$_9$wherein $R_9$ is ($C_1$–$C_6$)alkyl, ($C_2$–$C_6$)alkenyl, cycloalkyl, cycloalkyl ($C_1$–$C_6$)alkyl-, phenyl, heterocyclyl, phenyl($C_1$–$C_6$)alkyl-, heterocyclyl($C_1$–$C_6$)alkyl-, ($C_1$–$C_6$)alkoxy($C_1$–$C_6$)alkyl-, ($C_1$–$C_6$)alkoxy($C_1$–$C_6$)alkoxy($C_1$–$C_6$)alkyl-, any of which may be substituted on a ring or non-ring carbon atom or-on a ring heteroatom, if present. Examples of such $R_9$ groups include methyl, ethyl, n-and iso-propyl, n-, sec- and tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methyl piperidin-4-yl, 1-methylcyclopent-1-yl, adamantyl, tetrahydrofuran-3-yl and methoxyethyl.

Presently preferred are compounds of formula (I) wherein $R_4$ is a carboxylate ester of formula —(C=O)OR$_9$, wherein $R_9$ is benzyl, cyclopentyl, isopropyl or tert-butyl.

Specific examples of compounds useful as antibacterial-agents in accordance with the invention include those of the preparative examples herein, and pharmaceutically or veterinarily acceptable salts thereof.

Compounds of formula (I) may be prepared as described in WO 98/11063.

Salts of the compounds for use in accordance with the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

Compositions with which the invention is concerned may be prepared for administration by any route consistent with the pharmacokinetic properties of the active irigredient(s).

Orally administrable-compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants.for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for exarmple methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

In the hospital setting to combat severe bacterial infections, the active ingredient may be administered by intravenous infusion.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds set out in the following Table, representative of the compounds of formula (I) with which WO 98/11063 is concemed, were prepared. $^1$H and $^{13}$C NMR spectra were recorded using either a Bruker DPX250 spectrometer at 250.1 and 62.9 MHz respectively, or a Bruker AMX2 500 spectrometer at 500.1 and 125.7 MHz respectively. Mass spectra were obtained on a PE-SCIEX API 165 with a turbo ion spray interface. Infra red spectra were obtained on a Perkin Elmer 1600 series FTIR machine.

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 1 | (Chiral structure) | 5 | — | — | — |
| 2 | (Chiral structure) | — | — | 5 | m.p. 198–203° C. $^1$H-NMR: δ (CD$_3$OD), 8.23(1H, d, J=8.7Hz), 4.22(1H, d, J=8.1Hz), 4.05(2H, q, J=7.1Hz), 2.58(1H, ddd, J=10.8, 3.5Hz), 2.13 (1H, m), 1.47–1.31(2H, m), 1.26(3H, t, J=7.1Hz), 1.02(1H, m), 0.95(3H, t, J=6.9Hz), 1.02(9H, s), 0.80(3H, d, J=6.4Hz) and 0.72(3H, d, J=6.4Hz). $^{13}$C-NMR: δ (CD$_3$OD), 179.3, 176.8, 174.6, 65.1, 65.0, 64.3, 44.5, 44.4, 37.1, 29.7, 29.3, 26.8, 24.2, 19.4 and 16.9. IR (KBr disc): 3285, 3075, 2967, 2875, 1727, 1628, 1551, 1468, 1386, 1335, 1222, 1175, 1106, 1039 and 953 cm$^{-1}$. |
| 3 | (Chiral structure) | 14 | — | — | — |

-continued

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 4 | Chiral structure | 18 | — | — | — |
| 5 | Chiral structure | 7 | — | — | — |
| 6 | Chiral structure | 8 | — | — | — |

-continued

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 7 | Chiral structure | 9 | — | — | — |
| 8 | Chiral structure | 10 | — | — | — |
| 9 | Chiral structure | 11 | — | — | — |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 10 | Chiral (benzyl ester, tert-butyl, leucine, hydroxamic acid structure) | — | — | 8 | $^{1}$H-NMR; δ (CD$_3$OD), 8.10(1H, d, J=8.9Hz), 7.29–7.20(5H, m), 5.05(2H, s), 4.28(1H, d, J=8.9Hz), 3.87(1H, d, J=7.2Hz), 2.83–2.74(1H, m), 1.54–1.47(1H, m), 1.45–1.31(1H, m), 1.08–0.99(1H, m), 0.88(9H, s), 0.75 (3H, d, J=6.5Hz). |
| 11 | Chiral (isopropyl ester, phenyl, leucine, hydroxamic acid structure) | — | — | 8 | $^{1}$H-NMR; δ (CD$_3$OD), 7.14(5H, m), 5.15(1H, dd, J=11.84, 4.84Hz), 4.93 (1H, m), 4.00(1H, d, J=4Hz), 3.26(1H, dd, J=14.44, 4.75Hz), 3.10(1H, m), 2.95(1H, dd, J=14.42, 11.62Hz), 2.88(3H, s), 1.46(1H, dt, J=10.48, 3.78Hz), 1.15(6H, d, J=6.6Hz), 1.15(1H, m), 0.96(1H, m), 0.60(3H, d, J=6.2Hz) and 0.50(3H, d, J=6.2Hz). $^{13}$C-NMR; δ (CD$_3$OD), 176.5 171.6, 161.8, 138.6, 130.6, 130.1, 129.5, 127.8, 72.9, 70.5, 43.2, 36.9, 35.4, 34.3, 26.2, 24.2, 22.2 and 22.00. |
| 12 | Chiral (cyclopentyl ester, phenyl, propargyl, hydroxamic acid structure) | 38 | — | — | — |

-continued

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 13 | Chiral structure | — | — | 8 | $^1$H-NMR; δ (CD$_3$OD), 4.53(1H, t, J=4.4Hz), 4.27–4.15(2H, q), 4.00(1H, d, J=7.1Hz), 3.96–3.75(2H, m), 2.91–2.77(1H, m), 1.27(3H, t, J=7.2Hz), 1.21–1.12(1H, m), 0.95(3H, d, J=6.5Hz) and 0.91(3H, d, J=6.4Hz). |
| 14 | Chiral structure | — | — | 8 | $^1$H-NMR; δ (CD$_3$OD), 7.39–7.23(5H, m), 5.07(2H, s), 4.46–4.41(1H, dd, J=9.0, 5.0Hz), 3.99(1H, d, J=6.8Hz), 3.69(3H, s), 3.11(2H, t, J=6.5Hz), 2.91–2.76(1H, m), 1.92–1.35(8H, bm), 1.28–1.13(1H, m), 0.94(3H, d, J=6.5Hz) and 0.90(3H, d, J=6.4Hz). |
| 15 | Chiral structure | — | — | 8 | $^1$H-NMR; δ (CD$_3$OD), 8.28(1H, d, J=7.3Hz), 7.53(1H, d, J=7.4Hz), 7.31 (1H, d, J=7.7Hz), 7.15(1H, s), 7.13–6.96(2H, m), 4.78–4.67(1H, m), 4.08–3.96(3H, m), 3.23(2H, d, J=6.7Hz), 2.88–2.77(1H, m), 1.65–1.46(2H, m), 1.20–1.09(1H, m), 1.09(3H, t, J=7.1Hz), 0.89(3H, d, J=6.4Hz) and 0.89 (3H, d, J=6.4Hz). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 16 | Chiral (cyclopentyl ester, benzyl, alkyne-phenyl-Cl, hydroxamic acid structure) | 42 | — | — | — |
| 17 | Chiral (ethyl ester, SH, isobutyl, hydroxamic acid structure) | — | — | 8 | ¹H-NMR; δ (CD₃OD), 4.79–4.73(1H, m), 4.36–4.14(2H, q), 4.03(1H, d, J=6.9Hz), 3.28–3.02(2H, m), 2.92–2.76(1H, m), 1.78–1.54(2H, m), 1.28 (3H, t, J=7.2Hz), 1.26–1.12(1H, m), 0.93(3H, d, J=6.5Hz) and 0.90(3H, d, J=6.4Hz). |
| 18 | Chiral (tert-butyl ester, isobutyl, hydroxamic acid structure) | — | — | 8 | ¹H-NMR; δ (CD₃OD), 4.38–4.34(1H, dd, J=8.6, 6.6Hz), 3.97(1H, d, J=6.9Hz), 2.85–2.71(1H, m), 1.82–1.51(5H, br m), 1.46(9H, s), 1.26–1.10 (1H, m), 0.94(3H, d, J=6.6Hz) and 0.90(1H, d, J=6.5Hz). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 19 | Chiral structure with NH₂, t-Bu ester, hydroxamic acid, isobutyl | — | — | 8 | ¹H-NMR; δ (CD₃OD), 4.39–4.33(1H, dd, J=9.7, 4.5Hz), 4.00(1H, d, J=6.6Hz), 2.91–2.78(1H, m), 2.29(2H, t, J=6.9Hz), 2.24–2.08(1H, m), 1.96–1.81(1H, m), 1.77–1.53(2H, m), 1.47(9H, s), 0.95(3H, d, J=6.5Hz) and 0.91(3H, d, J=6.5Hz). |
| 20 | Chiral structure with p-OH phenyl, ethyl ester, hydroxamic acid, isobutyl | — | — | 8 | ¹H-NMR; δ (CD₃OD), 7.03(2H, d, J=8.5Hz), 6.69(2H, d, J=8.5Hz), 4.61 (1H, t, J=6.9Hz), 4.14–4.06(2H, q), 4.00(1H, d, J=6.4Hz), 2.97(2H, d, J=6.9Hz), 2.85–2.72(1H, m), 1.66–1.41(2H, m), 1.28–1.13(1H, m), 1.18 (3H, t, J=7.1Hz), 0.90(3H, d, J=6.5Hz) and 0.86(3H, d, J=6.5Hz) |
| 21 | Chiral structure with diethyl malonate, hydroxamic acid, isobutyl | — | — | 8 | ¹H-NMR; δ (CD₃OD), 5.14(1H, s), 4.32–4.16(4H, m), 4.03(1H, d, J=6.6Hz), 2.97–2.83(1H, m), 1.73–1.50(2H, m), 1.28(6H, m), 0.94(3H, d, J=6.5Hz) and 0.90(3H, d, J=6.4Hz). |

-continued

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 22 | Chiral (structure with t-butyl ester, benzyl, leucyl hydroxamate) | — | — | 8 | ¹H-NMR; δ (CD₃OD), 7.52–7.15(5H, m), 4.60(1H, t, J=7.1Hz), 4.00(1H, d, J=6.5Hz), 3.02(2H, d, J=7.1Hz), 2.85–2.72(1H, m), 1.67–1.46(2H, m), 1.37(9H, s), 1.27–1.10(1H, m), 0.91(3H, d, J=6.5Hz) and 0.87(3H, d, J=6.4Hz). |
| 23 | Chiral (structure with benzyl ester, benzyl, leucyl hydroxamate) | — | — | 8 | ¹H-NMR; δ (CD₃OD), 7.38–7.12(10H, m), 5.08(2H, s), 4.75(1H, t, J=7.0Hz), 3.98(2H, d, J=6.6Hz), 3.05(2H, d, J=7.0Hz), 2.84–2.71(1H, m), 1.62–1.38(2H, m), 1.24–1.07(1H, m), 0.85(3H, d, J=6.5Hz) and 0.81(3H, d, J=6.5Hz). |
| 24 | Chiral (structure with allyl ester, isobutyl, leucyl hydroxamate) | — | — | 8 | ¹H-NMR; δ (CD₃OD), (6.04–5.85), 6.04–5.85(1H, m), 5.40–5.18(2H, m), 4.60(2H, d, J=5.8Hz), 4.55–4.49(1H, dd, J=9.0, 5.6Hz), 3.98(1H, d, J=7.1Hz), 2.89–2.74(1H, m), 1.86–1.52(5H, br m), 1.27–1.12(1H, m) and 1.01–0.83(12H, m). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 25 | Chiral | — | — | 8 | ¹H-NMR; δ (CD₃OD), 4.53–4.48(1H, dd, J=9.3, 5.0Hz), 4.23–4.06(4H, m), 3.97(1H, d, J=7.2Hz), 2.89–2.73(1H, m), 2.50–2.39(2H, m), 2.25–2.09(1H, m), 2.01–1.86(1H, m), 1.74–1.52(2H, m), 1.27–1.24(6H, m), 1.25–1.11(1H, m), 0.94(3H, d, J=6.5Hz) and 0.90(3H, d, J=6.5Hz). |
| 26 | Chiral | — | — | 8 | ¹H-NMR; δ (CD₃OD), 7.38–7.28(10H, m), 5.17–5.03(4H, m), 4.94(1H, t, J=6.1Hz), 3.97(1H, d, J=6.9Hz), 2.91(2H, d, J=6.1Hz), 2.83–2.68(1H, m), 1.69–1.44(2H, m), 1.23–1.05(1H, m) and 0.82(6H, t, J=6.1Hz). |

-continued

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 27 | Chiral | — | — | 8 | ¹H-NMR; δ (CD₃OD), 7.40–7.28(5H, m), 5.14(2H, d, J=1.7Hz), 4.57–4.51 (1H, dd, J=9.3, 5.9Hz), 3.94(1H, d, J=7.4Hz), 2.85–2.72(1H, m), 1.83–1.43(5H, br m), 1.18–1.04(1H, m) and 0.93–0.83(12H, m). |
| 28 | Chiral | — | — | 8 | ¹H-NMR; δ (CD₃OD), 7.38–7.22(5H, m), 6.97(2H, d, J=8.5Hz), 6.65(2H, d, J=8.5Hz), 5.06(2H, s), 4.73–4.60(1H, m), 3.98(1H, d, J=6.8Hz), 2.97 (2H, d, J=7.0Hz), 2.85–2.72(1H, m), 1.64–1.34(2H, m), 1.21–1.06(1H, m), 0.84(3H, d, J=6.5Hz) and 0.82(3H, d, J=6.5Hz) |
| 29 | Chiral | — | — | 8 | ¹H-NMR; δ (CD₃OD), 4.63–4.47(1H, m), 3.95(1H, d, J=7.5Hz), 3.71(3H, s), 3.66(3H, s), 2.88–2.75(1H, m), 2.54–2.40(2H, m), 2.28–2.11(1H, m), 2.02–1.85(1H, m), 1.73–1.52(2H, m), 1.25–1.06(1H, m), 0.93(3H, d, J=6.5Hz) and 0.90(3H, d, J=6.4Hz). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 30 | Chiral | — | — | 8 | ¹H-NMR; δ (CD₃OD), 4.50(1H, t, J=3.8Hz), 4.02(1H, d, J=6.8Hz), 3.77–3.72(1H, dd, J=8.9, 4.1Hz), 3.61–3.56(1H, dd, J=9.7, 3.7Hz), 2.90–2.78 (1H, m), 1.73–1.54(2H, m), 1.47(9H, s), 1.30–1.15(1H, m), 1.18(9H, s) and 0.92(6H, t, J=6.7Hz). |
| 31 | Chiral | — | — | 8 | ¹H-NMR; δ (CD₃OD), 7.38–7.15(5H, m), 4.67–4.62(1H, dd, J=7.2, 6.1Hz), 4.02(1H, d, J=6.9Hz), 3.76(2H, s), 3.71(3H, s), 2.94–2.69(3H, m), 1.72–1.53(2H, m), 1.30–1.12(1H, m), 0.93(3H, d, J=6.5Hz) and 0.90(3H, d, J=6.4Hz). |
| 32 | Cl Chiral | — | — | 8 | ¹H-NMR; δ (CD₃OD), 7.35–7.16(4H, m), 4.78–4.53(1H, m), 4.22–4.07 (2H, m), 3.97(0.5H, d, J=7.1Hz), 3.93(0.5H, d, J=7.2Hz), 3.25–2.88(2H, m), 2.85–2.61(1H, m), 1.68–1.49(2H, m), 1.30–1.16(3H, m), 1.10–0.97 (1H, m), 0.90(1.5H, d, J=6.5Hz), 0.85(1.5H, d, J=6.5Hz) and 0.75(3H, d, J=5.2Hz). |

-continued

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 33 | Chiral structure | — | — | 8 | $^1$H-NMR; δ (CD$_3$OD), 7.41–7.25(10H, m), 5.14(2H, d, J=3.7Hz), 5.10(2H, d, J=2.0Hz), 4.65–4.53(1H, q), 3.93(1H, d, J=7.7Hz), 2.84–2.71(1H, m), 2.55–2.44(2H, m), 2.30–2.12(1H, m), 2.06–1.84(1H, m), 1.58–1.38(2H, m), 1.18–1.01(1H, m) and 0.82(6H, t, J=6.5Hz). |
| 34 | Chiral structure | — | — | 8 | $^1$H-NMR; δ (CD$_3$OD), 4.37–4.28(1H, q), 3.97(1H, d, J=7.2Hz), 3.02(2H, t, J=6.4Hz), 2.86–2.72(1H, m), 1.80–1.56(6H, m), 1.54–1.33(2H, m), 1.46 (9H, s), 1.43(9H, s), 1.25–1.08(1H, m), 0.95(3H, d, J=6.4Hz) and 0.90 (3H, d, J=6.4Hz). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 35 | [structure: chiral compound with 4-hydroxyphenyl, tert-butyl ester, leucine, hydroxamic acid] | — | — | 8 | $^1$H-NMR; δ (CD$_3$OD), 7.05(2H, d, J=8.5Hz), 6.69(2H, d, J=8.5Hz), 4.51 (1H, t, J=7.1Hz), 3.99(1H, d, J=6.8Hz), 2.93(2H, d, J=7.1Hz), 2.85–2.72 (1H, m), 1.67–1.42(2H, m), 1.37(9H, s), 1.23–1.09(1H, m), 0.91(3H, d, J=6.4Hz) and 0.87(3H, d, J=6.4Hz). |
| 36 | [structure: chiral compound with 4-tert-butoxyphenyl, tert-butyl ester, leucine, hydroxamic acid] | — | — | 8 | $^1$H-NMR; δ (CD$_3$OD), 7.16(2H, d, J=8.5Hz), 6.90(2H, d, J=8.5Hz), 4.55 (1H, t, J=7.2Hz), 3.99(1H, d, J=6.9Hz), 3.04–2.95(2H, m), 2.85–2.73(1H, m), 1.68–1.46(2H, m), 1.36(9H, s), 1.31(9H, s), 1.24–1.09(1H, m), 0.91 (3H, d, J=6.5Hz) and 0.87(3H, d, J=6.4Hz) |
| 37 | [structure: chiral compound with methylthioethyl, tert-butyl ester, leucine, hydroxamic acid] | — | — | 8 | $^1$H-NMR; δ (CD$_3$OD), 4.56–4.48(1H, dd, J=4.7, 9.1Hz), 3.95(1H, d, J=7.6Hz), 2.87–2.73(1H, m), 2.68–2.41(2H, m), 2.07(3H, s), 2.05–1.82 (2H, m), 1.72–1.52(2H, m), 1.23–1.07(1H, m), 0.94(3H, d, J=6.5Hz) and 0.90(3H, d, J=6.4Hz). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 38 | Chiral | — | — | 8 | ¹H-NMR; δ (CD₃OD), 7.39–7.15(10H, m), 5.15(2H, d, J=1.7Hz), 4.70 (1H, t, J=7.1Hz), 4.00(1H, d, J=7.1Hz), 3.72(2H, s), 2.93–2.69(3H, m), 1.73–1.44(2H, m), 1.23–1.08(1H, m) and 0.85(6H, t, J=7.0Hz). |
| 39 | Chiral | — | — | 8 | ¹H-NMR; δ (CD₃OD), 5.08–4.93(1H, m), 4.64–4.51(1H, dd, J=4.6, 9.2Hz), 3.96(1H, d, J=7.6Hz),2.87–2.75(1H, m), 2.71–2.44(2H, m), 2.08 (3H, s), 2.04–1.86(1H, m), 1.75–1.52(2H, m), 1.32–1.21(6H, m), 1.20–1.07(1H, m) 0.95(3H, d, J=6.4Hz) and 0.90(3H, d, J=6.4Hz). |
| 40 | Chiral | — | — | 8 | ¹H-NMR; δ (CD₃OD), 4.27–4.16(1H, m), 3.96(1H, d, J=7.2Hz), 2.90–2.76 (1H, m), 1.85–1.51(8H, m), 1.46(9H, s), 1.35–1.02(6H, m), 0.93(3H, d, J=6.5Hz) and 0.89(3H, d, J=6.5Hz). |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 41 | Chiral (structure with tert-butyl ester) | — | — | 8 | $^1$H-NMR; δ (CD$_3$OD), 9.20(1H, s), 8.10(1H, d, J=4.9Hz), 7.32–7.18(5H, m), 5.42(1H, d, J=7.0Hz), 5.05(1H, d, J=6.5Hz), 4.17(1H, br s), 3.41 (1H, t, J=6.7Hz), 1.86–1.45(3H, m), 1.39(9H, s) and 0.95(6H, t, J=7.3Hz). $^{13}$C-NMR; δ (CDCl$_3$), 175.0, 170.1, 168.9, 137.0, 129.1, 128.5, 127.0, 83.7, 73.2, 57.6, 44.2, 39.0, 28.2, 26.1, 23.1 and 22.7. |
| 42 | Chiral (structure with cyclopentyl ester) | — | 1b | 8 | — |
| 43 | Chiral (structure with cyclopentyl ester) | — | 1a | 8 | — |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 44 | Chiral | — | — | 8 | $^1$H-NMR; δ (CD$_3$OD), 7.2(5H, m), 5.8(1H, m), 5.0(3H, m), 4.6(1H, t, J=7.1Hz), 4.1(1H, d, J=6.2Hz), 3.0(2H, m), 2.8(1H, m), 2.4(2H, m) and 1.9–1.2(10H, m). $^{13}$C-NMR; δ (MeOD); 25.0, 33.8, 33.9, 34.9, 39.2, 50.8, 55.8, 72.8, 80.0, 118.1, 128.3, 130.3, 130.8, 138.3, 171.9, 173.2 and 175.5. LRMS: [M + Na] 427.2, [M − H] = 403.0 |
| 45 | Chiral | — | — | 8 | $^1$H-NMR; δ (CD$_3$OD), 7.2(10H, m), 5.0(1H, m), 4.55(1H, m), 4.05(1H, d), 3.3(2H, m), 2.95(3H, m), 2.85(2H, m) and 1.55(8H, m). $^{13}$C-NMR; δ (CD$_3$OD), 173.1, 170.6, 169.9, 138.0, 136.0, 128.6, 128.3, 127.7, 126.1, 125.7, 77.8, 70.5, 53.5, 50.5, 37.2, 34.3, 33.2, 31.6, 31.5 and 22.7. LRMS: [M + Na] = 477.2, [M − H] = 453.0 |
| 46 | Chiral | — | — | 8 | $^1$H-NMR; δ (CD$_3$OD), 7.6(1H, m), 7.3(5H, m), 5.1(1H, m), 4.6(1H, m), 4.0(1H, m), 3.3(1H, m), 3.0(2H, m), 2.7(1H, m) and 2.0–0.8(15H, m). $^{13}$C-NMR; δ (CD$_3$OD), 176.8, 173.2, 172.0, 138.4, 130.8, 130.3, 128.3, 80.0, 74.3, 73.4, 55.5, 50.9, 39.1, 33.9, 33.4, 25.0, 21.9 and 14.8. LRMS: M + Na = 429.4, M − H = 405.0 |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 47 | Chiral | — | — | 7 | $^{1}$H-NMR; δ (CD$_3$OD), 7.17(10H, m), 5.01(1H, m), 4.51(1H, t), 2.97(4H, br m), 2.68(1H, m), 2.22(2H, br m) and 1.55(8H, br m). $^{13}$C-NMR; δ (CD$_3$OD), 25.0, 33.8, 33.9, 36.1, 39.2, 39.3, 45.9, 55.8, 79.8, 127.9, 128.2, 129.8, 129.9, 130.5, 130.8, 138.5, 140.5, 171.0, 172.9 and 176.5. |
| 48 | Chiral | — | — | 7 | $^{1}$H-NMR; δ (CD$_3$OD), 7.22(5H, m), 5.12(1H, s), 4.26(1H, m), 3.02(2H, br m), 2.66(1H, m), 2.35(1H, m), 1.67(8H, br m) and 1.33 (3H, d). $^{13}$C-NMR; δ (CDCl$_3$), 18.5, 24.1, 32.9, 33.0, 35.2, 38.9, 45.6, 48.9, 78.9, 127.2, 129.0, 129.4, 138.6, 172.7 and 174.0. |
| 49 | Chiral | — | — | 8 | $^{1}$H-NMR; δ (CD$_3$OD), 7.3(10H, m), 5.3(1H, s), 5.11(1H, m), 4.05(1H, m), 3.3(2H, m), 3.15(1H, m), 2.9(2H, m) and 1.55(8H, m). $^{13}$C-NMR; δ (CD$_3$OD), 175.4, 172.1, 171.8, 140.2, 137.9, 130.6, 130.1, 129.9, 129.7, 128.9, 128.0, 80.4, 72.7, 58.6, 52.4, 36.5, 33.7, 24.9 and 24.8. |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 50 | Chiral (structure) | — | — | 8 | $^1$H-NMR; δ (CD$_3$OD), 7.40(5H, m), 5.40(1H, s), 5.18(1H, m), 4.00(1H, d, J=13.25Hz), 2.82(1H, m) and 2.00–0.98(19H, series of m). $^{13}$C-NMR; δ (CD$_3$OD), 176.3, 172.2, 172.0, 137.0, 130.19, 129.9, 129.2, 80.3, 73.6, 59.1, 50.6, 39.1, 36.9, 34.7, 33.5, 31.3, 26.7, 26.5, 25.0 and 24.9. LRMS: [M − 1] = 431 and [M + Na] = 455. |
| 51 | Chiral (structure) | — | — | 8 | $^1$H-NMR; δ (CD$_3$OD), 7.4–7.11(10H, br m), 6.45(1H, d, J=15.8Hz), 6.32 (0.85H, m), 6.12(0.15H, m), 5.43(0.15H, s), 5.39(0.85H, s), 5.17(0.15H, m), 5.09(0.85H, m), 4.29(0.15H, d, J=5.3Hz), 4.13(0.85H, d, J=6.8Hz), 2.97(1H, m), 2.65–2.35(2H, m), and 1.85–1.28(8H, m). $^{13}$C-NMR; δ (CD$_3$OD), 175.6, 172.0, 171.9, 139.2, 137.7, 134.0, 130.2, 129.8, 129.6, 128.9, 128.3, 127.6, 80.4, 73.0, 58.6, 50.6, 34.2, 33.7 and 24.8. LRMS: [M + H] = 467.2 [M + Na] = 489.2 [M − H] = 465.0. |
| 52 | Chiral (structure) | — | — | 8 | $^1$H-NMR; δ (CD$_3$OD), 7.40–7.28(5H, m), 5.42(1H, s), 5.18–5.14(1H, m), 5.09–4.91(5H, s), 4.15–4.05(1H, d),3.10–3.02(1H, m), 2.43–2.21(2H, m) and 1.89–1.53(11H, m). $^{13}$C-NMR; δ (CD$_3$OD), 175.6, 172.1, 143.7, 137.9, 130.2, 129.8, 129.0, 128.7, 114.1, 80.4, 72.9, 58.7, 48.8, 38.5, 33.8, 25.0, 24.9 and 22.8. LRMS [M + H] = 405 [M − H] = 403 |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 53 | Chiral structure with 4-hydroxyphenyl group, cyclopentyl ester, isobutyl and hydroxy substituents, hydroxamic acid | — | — | 8 | $^1$H-NMR; δ (CD$_3$OD), 7.20(2H, d, J=8.6Hz), 6.76(2H, d, J=8.5Hz), 5.24 (1H, s), 5.15(1H, m), 3.96(1H, d, J=7.4Hz), 2.85(1H, m), 1.84–1.56 (10H, br m), 1.15(1H, m), 0.96(3H, d, J=6.4Hz) and 0.91(3H, d, J=6.4Hz). $^{13}$C-NMR; δ (CD$_3$OD), 176.2, 172.6, 171.9, 159.3, 130.5, 128.1, 116.9, 80.1, 73.7, 58.8, 49.4, 39.5, 33.8, 27.0, 24.9, 24.4 and 22.5. LRMS: [M + Na] = 445.2, [M + H] = 423.2, [M − H] = 421.0 |
| 54 | Chiral structure with 3-nitrophenyl group, cyclopentyl ester, isobutyl and hydroxy substituents, hydroxamic acid | — | — | 8 | $^1$H-NMR; δ (CD$_3$OD), 8.33(0.5H, s), 8.29(0.5H, s), 8.20(1H, m), 7.83 (1H, m), 7.61(1H, m), 5.23(1H, m), 4.71(1H, m), 4.02(0.5H, d, J=6.9Hz), 3.98(0.5H, d, J=7.3Hz), 2.91(1H, m), 1.91–1.41(10H, br m), 1.21(1H, m), 0.96(1.5H, d, J=6.5Hz), 0.91(3H, m) and 0.83(1.5H, d, J=6.7Hz). $^{13}$C-NMR; δ (CD$_3$OD), 175.9, 149.8, 134.9, 131.0, 124.1, 123.6, 123.3, 80.6, 73.4, 57.6, 39.1, 33.4, 26.9, 24.5, 23.8 and 22.2. LRMS: [M + Na] = 474.0, [M − H] = 450.0 |
| 55 | Chiral structure with 3-aminophenyl group, cyclopentyl ester, isobutyl and hydroxy substituents, hydroxamic acid | — | — | 8 | $^1$H-NMR; δ (CD$_3$OD), 7.07(1H, m), 6.73(1H, m), 6.68(1H, m), 5.26 (0.5H, s), 5.25(0.5H, s), 5.16(1H, m), 4.71(1H, m), 4.04(0.5H, d, J=6.3Hz), 4.00(0.5H, d, J=6.8Hz), 2.88(1H, m), 1.88–1.47(10H, br m), 0.95(1.5H, d, J=6.3Hz), 0.89(3H, m) and 0.86(1.5H, d, J=6.6Hz). $^{13}$C-NMR; δ (CD$_3$OD), 175.8, 172.1, 171.6, 149.4, 138.3, 130.5, 118.1, 116.5, 115.4, 80.0, 73.4, 58.7, 39.3, 33.3, 26.8, 24.6, 23.9 and 22.2. LRMS: [M + H] = 422.2, [M − H] = 420.0 |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 56 | Chiral (structure) | — | — | 7 | $^1$H-NMR; δ (CD$_3$OD), 7.38(5H, m), 5.35(1H, s), 5.17(1H, m), 2.94(1H, m), 2.27(2H, m), 1.54(10H, br m), 1.15(1H, m) and 0.9843(6H, m). $^{13}$C-NMR; δ (CD$_3$OD), 177.2, 171.8, 170.6, 137.3, 129.8, 129.5, 128.8, 79.9, 58.8, 42.6, 41.6, 36.9, 33.3, 26.8, 24.5, 23.6 and 22.4. |
| 57 | Chiral (structure) | — | — | 8 | $^1$H-NMR; δ (CD$_3$OD), 5.18(1H, m), 4.30(1H, d, J=6.4Hz), 3.98(1H, d, J=7.3Hz), 3.31(1H, m), 2.88(1H, m), 1.88–1.46(16H, m), 1.29–1.06(6H, m), 0.94(3H, d, J=6.4Hz) and 0.87(3H, d, J=6.4Hz). $^{13}$C-NMR; δ (CD$_3$OD), 176.3, 173.2, 172.0, 79.7, 73.6, 59.3, 41.8, 39.5, 33.9, 31.0, 27.5, 27.2, 25.0, 24.6 and 22.5. LRMS: [M + H]$^+$ 413.2 |
| 58 | Chiral (structure) | — | — | 8 | $^1$H-NMR; δ (CD$_3$OD), 7.41(5H, m), 5.42(1H, s), 4.81(1H, m), 4.00(1H, d, J=7.5Hz), 2.91(1H, m), 2.08–1.10(13H, m), 0.97(3H, d, J=6.4Hz) and 0.92(3H, d, J=6.4Hz). $^{13}$C-NMR; δ (CD$_3$OD), 176.2, 171.9, 171.8, 137.7, 130.2, 129.8, 128.9, 75.5, 73.6, 59.1, 49.4, 39.5, 32.7, 32.3, 27.2, 27.0, 24.8, 24.7 and 22.5. LRMS: [M + Na] = 443.0, [M − H]$^-$ = 419.0 |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 59 | Chiral (structure) | — | — | 8 | $^1$H-NMR; δ (CD$_3$OD), 7.39(5H, m), 5.41(1H, s), 5.40(1H, s), 4.71(1H, m), 3.97(1H, d, J=7.5Hz), 2.86(1H, m), 2.08–1.37(8H, br m), 1.18(2H, m) and 0.92(9H, m). $^{13}$C-NMR; δ (CD$_3$OD), 176.3, 172.3, 171.9, 137.8, 130.2, 129.9, 129.2, 85.6, 73.7, 59.2, 49.1, 41.6, 39.5, 33.6, 32.8, 27.1, 24.5, 23.7, 22.5 and 18.9. LRMS: [M − H] = 443.0, [M − H] = 419.0 |
| 60 | Chiral (structure) | — | — | 8 | $^1$H-NMR; δ (CD$_3$OD), 8.36(1H, d), 5.18(1H, m), 4.26(1H, m), 3.97(1H, d, J=7.3Hz), 2.82(1H, m), 2.31(1H, m), 1.88–1.08(19H, m), 0.95(3H, d, J=6.4Hz) and 0.90(3H, d, J=6.4Hz). LRMS [M + Na] = 421.2, [M − H] = 397.2 |
| 61 | Chiral (structure) | — | — | 7 | $^1$H-NMR; δ (CD$_3$OD), 7.25(5H, m), 5.1(1H, m), 4.6(1H, t), 3.05(2H, m), 2.85(1H, m), 2.05(1H, t), 1.45–1.9(10H, m), 1.05–1.2(1H, m), and 0.8–0.95(6H, m). $^{13}$C-NMR δ (CD$_3$OD), 177.5, 173.2, 170.9, 138.6, 130.8, 129.9, 128.2, 79.9, 55.6, 42.4, 42.2, 39.0, 37.4, 33.9, 27.3, 25.0, 24.2 and 22.7. LRMS: [M + H] = 405, [M + Na] = 427 [M − H] = 403 |

-continued
| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 62 | 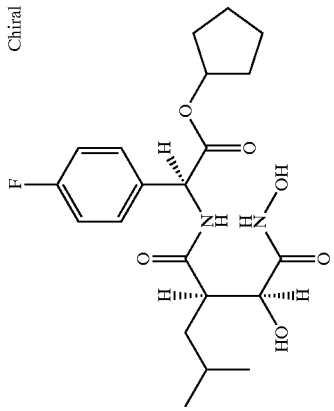 Chiral | — | — | 8 | $^1$H-NMR; δ (CD$_3$OD), 7.43(2H, m), 7.09(2H, m), 5.42(0.2H, s), 5.41 (0.8H, s), 5.17(1H, m), 4.02(0.2H, d, J=7.1Hz), 8(0.8H, d, J=7.5Hz), 2.88(1H, m) 1.90–1.55(10H, m), 0.96(2.4H, d, J=6.4Hz), 0.91(2.4H, J=6.4Hz), 0.85(1.2H, m) and 1.17(1H, m). $^{13}$C-NMR; δ (CD$_3$OD), 176.2, 171.9, 166.5, 162.6, 133.9, 131.1, 117.0, 116.7, 80.5, 73.7, 58.2, 49.4, 39.5, 33.8, 27.4, 24.9, 24.8 and 22.5. LRMS: [M + H] = 425.2, [M + Na] = 447.0, [M − H] = 422.8 |
| 63 | 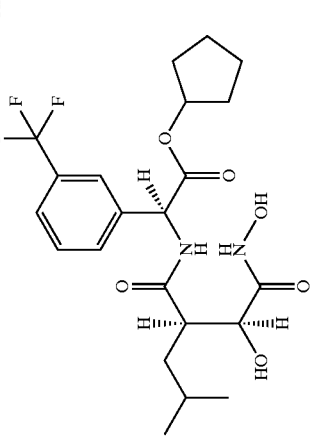 Chiral | — | — | 8 | $^1$H-NMR; δ (CD$_3$OD), 7.70(4H, br m), 5.58(1H, s), 5.19(1H, m), 4.01 (1H, d, J=7.5Hz), 2.93(1H, m), 1.86–1.51(10H, br m), 1.20(1H, m), 0.90 (3H, d, J=6.4Hz) and 0.81(3H, d, J=6.5Hz). $^{13}$C-NMR; δ (CD$_3$OD), 179.4, 175.1, 174.6, 143.4, 136.2, 134.3, 129.8, 128.8, 84.1, 76.9, 61.6, 52.9, 42.7, 37.0, 30.6, 28.1 and 25.7. LRMS: [M + H] = 475.2, [M + Na] = 497.0, [M − H] = 473.0. |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 64 | Chiral (structure with CF₃-phenyl, cyclopentyl ester, hydroxamic acid) | — | — | 8 | $^1$H-NMR; δ (CD$_3$OD), 7.74–7.4(4H, m), 5.80(1H, s), 5.16(1H, m), 4.01 (0.125H, m), 3.95(0.875H, d, J=7.6Hz), 2.84(1H, m), 1.86–1.49(10H, br m), 1.17(1H, m), 0.96(2.6H, d, J=6.4Hz), 0.91(2.6H, d, J=6.4Hz) and 0.84(0.75H, m). $^{13}$C-NMR; δ (CD$_3$OD), 19.9, 22.5, 24.1, 24.8, 24.9, 27.0, 33.7, 33.8, 39.6, 49.3, 55.6, 73.6, 80.2, 127.8, 128.4, 129.9, 132.2, 136.2, 138.8, 172.0, 172.6 and 176.3. LRMS: [M + H] = 475.2, [M + Na] = 497.2, [M − H] = 472.8 |
| 65 | Chiral (structure with methyl-phenyl, cyclopentyl ester, hydroxamic acid) | — | — | 8 | $^1$H-NMR; δ (CD$_3$OD), 0.91(3H, d, J=6.4Hz), 0.95(3H, d, J=6.4Hz), 1.08–1.20(1H, m), 1.53–1.85(10H, m), 2.41(3H, s), 2.79–2.88(1H, m), 3.96 (1H, d, J=7.7Hz), 5.17–5.22(1H, m), 5.63(1H, s) and 7.16–7.22(4H, m). $^{13}$C-NMR; δ (CD$_3$OD), 19.9, 22.5, 24.1, 24.8, 24.9, 27.0, 33.7, 33.8, 39.6, 49.3, 55.6, 73.6, 80.2, 127.8, 128.4, 129.9, 132.2, 136.2, 138.8, 172.0, 172.6 and 176.3. LRMS: [M + Na] = 443.2 |
| 66 | Chiral (structure with phenyl, cyclopentyl ester, cyclopentylmethyl, hydroxamic acid) | — | — | 8 | $^1$H-NMR; δ (CD$_3$OD), 1.93–1.05(19H, br m), 2.78–2.69(1H, m), 3.05(2H, d, J=7.1Hz), 4.02(1H, d, J=6.5Hz), 4.64(1H, t, J=7.2Hz), 5.11–5.06(1H, m) and 7.30–7.11(5H, m). $^{13}$C-NMR; δ (CD$_3$OD), 25.0, 26.4, 26.5, 33.6, 33.8, 33.9, 34.5, 37.0, 39.1, 39.2, 50.9, 55.7, 73.7, 80.1, 128.3, 129.9, 130.8, 138.4, 171.9, 173.2 and 176.1. LRMS: [M + Na] = 469.2 |

| EXAMPLE No. | MOL STRUCTURE | WO98/11063 EXAMPLE No. | WO99/46241 EXAMPLE No. | Prepared by analogy with WO 98/11063 Example No. | CHARACTERISING DATA |
|---|---|---|---|---|---|
| 67 | Chiral structure with cyclopentyl ester, phenyl, cyclohexylmethyl, and hydroxamic acid groups | — | — | 8 | ¹H-NMR; δ (CD₃OD), 7.48–7.28(5H, m), 5.40(1H, s), 5.19(1H, m), 3.99(1H, d, J=7.5Hz), 2.90(1H, m), 1.98–1.43(14H, m), 1.43–1.09(5H, m), and 1.09–0.78(2H, m). ¹³C-NMR: δ (CD₃OD), 176.3, 172.1, 172.0, 137.8, 130.2, 129.8, 129.1, 80.3, 73.7, 59.0, 48.5, 38.1, 36.5, 35.7, 34.1, 33.8, 28.1, 27.7, 27.6, 25.0 and 24.9. LRMS: [M + Na] = 469, [M − H] = 445 |
| 68 | Chiral structure with cyclopentyl ester, benzyl, isobutyl, and hydroxamic acid groups | — | — | 7 | ¹H-NMR; δ (CD₃OD), 0.74–0.72(5.3H, m), 0.83(0.7H, d, J=6.4Hz), 1.13–96(2H,m), 1.47–1.38(1H, m), 1.91–1.58(6H, br m), 2.07(1H, dd, J=8.6Hz), 2.26(0.9H, dd, J=14.3, 5.8Hz), 2.39(0.1H, dd, J=14.6, 6.2Hz), 2.56–2.48(0.1H, m), 2.83–2.71(0.9H, m), 2.91(1H, dd, J=13.9, 9.9Hz), 3.16(1H, dd, J=13.9, 5.5Hz), 4.62(1H, dd, J=9.8, 5.6Hz), 5.14(1H, m) and 7.31(5H, m). ¹³C-NMR: δ (CH₃OD), 22.5(p), 24.1(p), 25.0(s), 27.1 (t), 33.9(s), 37.5(s), 38.7(s), 42.1(s), 42.2(t), 55.6(t), 80.0(t), 128.2(t), 129.9(t), 130.6(t), 138.7(q), 170.9(q), 173.3(q) and 177.7(q). LRMS: [M + Na] = 427.2 |

BIOLOGICAL EXAMPLE

Minimal inhibitory concentrations (MIC) of inhibitors against E. coli strain DH5α (Genotype; F-φ80dlacZΔM15Δ(lacZYA-argF)U 169 deoR recA1 endA1 hsdR17($r_k^-$, $m_k^+$)phoA supE44λ⁻thi-1 gyrA96 relA1) obtained from GibcoBRL Life Technologies, or *Staphylococcus capitis* (American Type Culture Collection number 35661) were determined as follows. Stock solutions of each test compound were prepared by dissolution of the compound in dimethylsulfoxide at 10 mM. For the determination of the minimal inhibitory concentration, two fold serial dilutions were prepared in 2×YT broth (typtone 16 g/1, yeast extract 10 g/1, sodium chloride 5 g/1 obtained from BIO 101 Inc, 1070 Joshua Way, Vista, Calif. 92083, USA) to yield 0.05 ml compound-containing medium per well. Inocula were prepared from cultures grown overnight in 2×YT broth at 37° C. Cell densities were adjusted to absorbance at 660 nm ($A_{660}$)=0.1; the optical density-standardized preparations were diluted 1:1000 in 2×YT broth; and each well inoculated with 0.05 ml of the diluted bacteria. Microtiter plates were incubated at 37° C. for 18 hours in a humidified incubator. The MIC ($\mu$M) was recorded as the lowest drug concentration that inhibited visible growth.

Thus it was found, for example, that the MIC for the compound of structure

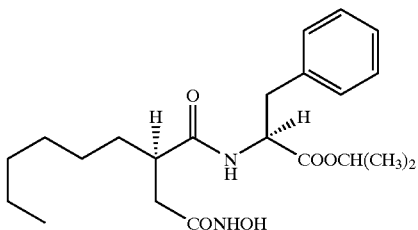

in pspect of *Staphylococcus capitis* was 100 $\mu$M.

What is claimed is:

1. A method for the treatment of bacterial infections in humans and non-human mammals, which comprises administering to a subject suffering such infection an antibacterial effective dose of a compound of formula (I):

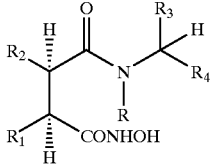

(I)

wherein:
$R_1$ represents hydrogen, hydroxy, amino, methyl, or trifluoromethyl;
$R_2$ represents a group $R_{10}$—$(X)_n$—(ALK)— wherein
$R_{10}$ represents hydrogen, a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, trifluoromethyl, cyano, nitro, —COOH, —$CONH_2$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$)alkyl group, and
ALK represents a straight or branched divalent $C_1$–$C_6$ alkylene, $C_2$–$C_6$ alkenylene, $C_2$–$C_6$ alkynylene radical, and may be interrupted by one or more non-adjacent —NH—, —O— or —S— linkages,
X represents —NH—, —O— or —S—, and
n is 0 or 1;
R represents hydrogen or $C_1$–$C_6$ alkyl,
$R_3$ represents the characterising group of a natural or non-natural a amino acid in which any functional groups may be protected; and
$R_4$ represents an ester or thioester group,
or a pharmaceutically acceptable salt, hydrate or solvate thereof.

2. The method as claimed in claim 1 wherein the stereochemical configuration at the carbon atom carrying the $R_3$ group is S.

3. The method as claimed in claim 1 wherein $R_1$ is hydrogen.

4. The method as claimed in claim 3 wherein $R_2$ is:
$C_1$–$C_6$ alkyl, $C_3$–$C_6$ alkenyl or $C_3$–$C_6$ alkynyl;
phenyl($C_1$–$C_6$ alkyl)-, phenyl($C_3$–$C_6$ alkenyl)-or phenyl ($C_3$–$C_6$ alkynyl)- optionally substituted in the phenyl ring;
cycloalkyl($C_1$–$C_6$ alkyl)-, cycloalkyl($C_3$–$C_6$ alkenyl)- or cycloalkyl($C_3$–$C_6$ alkynyl)- optionally substituted in the phenyl ring;
heterocyclyl($C_1$–$C_6$ alkyl)-, heterocyclyl($C_3$–$C_6$ alkenyl)- or heterocyclyl($C_3$–$C_6$ alkynyl)- optionally substituted in the heterocyclyl ring; or
4-phenylphenyl($C_1$–$C_6$ alkyl)-, 4-phenylphenyl($C_3$–$C_6$ alkenyl)-, 4-phenylphenyl($C_3$–$C_6$ alkynyl)-, 4-heteroarylphenyl($C_1$–$C_6$ alkyl)-, 4-heteroarylphenyl ($C_3$–$C_6$ alkenyl)-, 4-heteroarylphenyl($C_3$–$C_6$ alkynyl)-, optionally substituted in the terminal phenyl or heteroaryl ring.

5. The method as claimed in claim 3 wherein $R_2$ is methyl, ethyl, n- and iso-propyl, n- and iso-butyl, n-pentyl, isopentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofiran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

6. The method as claimed in claim 3 wherein $R_2$ is n-propyl, n-butyl, n-pentyl, benzyl or cyclopentylmethyl.

7. The method as claimed in claim 4 wherein R is hydrogen.

8. The method as claimed in claim 7 wherein $R_3$ is
$C_1$–$C_6$ alkyl, phenyl, 2,- 3-, or 4-hydroxyphenyl, 2,- 3-, or 4-methoxyphenyl, 2,- 3-, or 4-pyridylmethyl, benzyl, 2,- 3-, or 4-hydroxybenzyl, 2,- 3-, or 4-benzyloxybenzyl, 2,- 3-, or 4-$C_1$–$C_6$ alkoxybenzyl, or benzyloxy($C_1$–$C_6$alkyl)-; or $C_1$–$C_6$ alkyl, phenyl, 2,- 3-, or 4-hydroxyphenyl, 2,- 3-, or 4-methoxyphenyl, 2,- 3-, or 4-pyridylmethyl, 2,- 3-, or 4-hydroxybenzyl, 2,- 3-, or 4-benzyloxybenzyl, 2,- 3-, or 4-$C_1$–$C_6$ alkoxybenzyl, or benzyloxy($C_1$–$C_6$alkyl)-; or
the characterising group of a natural a amino acid, in which any functional group may be protected, any amino group may be acylated and any carboxyl group present may be amidated; or a group —(Alk)$R_7$ where Alk is a ($C_1$–$C_6$)alkyl or ($C_2$–$C_6$)alkenyl group optionally interrupted by one or more —O—, or —S— atoms or —N($R_{12}$)— groups, where $R_{12}$ is a hydrogen atom or a ($C_1$–$C_6$)alkyl group, n is 0 or 1, and $R_7$ is an optionally substituted cycloalkyl or cycloalkenyl group; or a benzyl group substituted in the phenyl ring by a group of formula —OCH$_2$CO$R_8$ where $R_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —C$R_a R_b R_c$ in which:
  each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or
  $R_c$ is hydrogen and $R_a$ and $R_b$ are independently phenyl or heteroaryl such as pyridyl; or
  $R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or
  $R_a$, $R_b$ and $R_c$ together with the carbon atom to which they are attached form a tricyclic ring; or
  $R_a$ and $R_b$ are each independently ($C_1$–$C_6$)alkyl, ($C_2$–$C_6$)alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —SO$_2$($C_1$–$C_6$)alkyl, —S($C_2$–$C_6$)alkenyl, —SO($C_2$–$C_6$)alkenyl, —SO$_2$($C_2$–$C_6$)alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$)alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl or benzyl.

9. The method as claimed in claim 7 wherein $R_3$ is methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, or 4-aminobutyl.

10. The method as claimed in claim 7 wherein $R_3$ is methyl, benzyl, tert-butyl, iso-butyl, phenyl or isopropyl.

11. The method as claimed in claim 8 wherein $R_4$ is a group of formula —(C=O)O$R_9$, —(C=O)S$R_9$, —(C=S)S$R_9$, and —(C=S)O$R_9$ wherein $R_9$ is ($C_1$–$C_6$)alkyl, ($C_2$–$C_6$)alkenyl, cycloalkyl, cycloalkyl($C_1$–$C_6$)alkyl-, phenyl, heterocyclyl, phenyl($C_1$–$C_6$)alkyl-, heterocyclyl($C_1$–$C_6$)alkyl-, ($C_1$–$C_6$)alkoxy($C_1$–$C_6$)alkyl-, or ($C_1$–$C_6$)alkoxy($C_1$–$C_6$)alkoxy($C_1$–$C_6$)alkyl-, any of which may be substituted on a ring or non-ring carbon atom or on a ring heteroatom, if present.

12. The method as claimed in claim 11 wherein $R_4$ is a group of formula —(C=O)O$R_9$ wherein $R_9$ is methyl, ethyl, n-or iso-propyl, n-, sec- or tert-butyl, 1-ethyl-prop-1-yl, 1-methyl-prop-1-yl, 1-methyl-but-1-yl, cyclopentyl, cyclohexyl, allyl, phenyl, benzyl, 2-, 3-and 4-pyridylmethyl, N-methylpiperidin4-yl, 1-methylcyclopent-1yl, adamantyl, tetrahydrofuran-3-yl or methoxyethyl.

13. The method as claimed in claim 11 wherein $R_4$ is a group of formula —(C=O)O$R_9$ wherein $R_9$ is benzyl, cyclopentyl, isopropyl or tert-butyl.

14. The method as claimed in claim 1 wherein R and $R_1$ are each hydrogen, $R_2$ is n-propyl, n-butyl, n-pentyl, benzyl or cyclopentylmethyl, $R_3$ is methyl, benzyl, tert-butyl, iso-butyl, phenyl or isopropyl, and wherein the stereochemical configuration at the carbon atom carrying the $R_2$ group is R.

* * * * *